United States Patent [19]

Kerwin

[11] Patent Number: 4,813,926

[45] Date of Patent: Mar. 21, 1989

[54] MEDICAL SUCTION DEVICE WITH AIR VENT AND FIXED RESTRICTOR

[75] Inventor: Michael J. Kerwin, Ballwin, Mo.

[73] Assignee: Sherwood Medical Company, St. Louis, Mo.

[21] Appl. No.: 188,695

[22] Filed: May 2, 1988

Related U.S. Application Data

[63] Continuation of Ser. No. 881,374, Jul. 2, 1986, abandoned.

[51] Int. Cl.$^4$ .............................................. A61M 1/00
[52] U.S. Cl. ............................... 604/118; 604/45; 604/902; 433/95; 433/100
[58] Field of Search ............... 604/30, 35, 45, 118, 604/119, 902; 433/91, 95, 96; 251/341, 342, 347; 15/335, 330, 361, 326, 344, 345, 375, 421

[56] References Cited

U.S. PATENT DOCUMENTS

| | | | |
|---|---|---|---|
| 152,071 | 6/1874 | Campbell . | |
| 2,449,497 | 9/1948 | McLeod | 128/276 |
| 2,531,730 | 11/1950 | Henderson | 433/91 |
| 3,071,402 | 1/1963 | Lasto et al. | 284/64 |
| 3,334,821 | 8/1967 | Garrison | 239/589 |
| 3,335,727 | 8/1967 | Spoto | 604/119 |
| 3,375,828 | 4/1968 | Sheridan | 128/351 |
| 3,568,318 | 3/1971 | Martin | 32/27 |
| 3,625,221 | 12/1971 | Corbett | 128/351 |
| 3,628,813 | 12/1971 | Lee, Jr. et al. | 285/31 |
| 3,645,497 | 2/1972 | Nyboer | 433/95 |
| 3,713,443 | 1/1973 | Fertik | 128/276 |
| 3,807,401 | 4/1974 | Riggle et al. | 604/902 |
| 3,828,780 | 8/1974 | Morrison, Jr. | 604/902 |
| 3,885,565 | 5/1975 | Satchell | 128/276 |
| 3,958,573 | 5/1976 | Wiley | 128/276 |
| 3,965,901 | 6/1976 | Penny et al. | 128/276 |
| 4,022,218 | 5/1977 | Riddick | 128/350 |
| 4,204,328 | 5/1980 | Kutner | 433/29 |
| 4,221,220 | 9/1980 | Hansen | 128/276 |
| 4,227,529 | 10/1980 | Lomholt | 433/96 |
| 4,299,221 | 11/1981 | Phillips et al. | 604/119 |
| 4,468,217 | 8/1984 | Kuzmick et al. | 604/48 |
| 4,540,406 | 9/1985 | Miles | 604/269 |
| 4,589,869 | 5/1986 | Wernborg | 604/119 |

OTHER PUBLICATIONS

NOW! Vacuum ONLY When You Need It With The New Argyle Selec-Trol ™ Yankauer Suction Tube (Brochure-ARGYLE).

Primary Examiner—C. Fred Rosenbaum
Assistant Examiner—J. L. Kruter
Attorney, Agent, or Firm—Stanley N. Garber; Andrew J. Beck; William R. O'Meara

[57] ABSTRACT

A fine tip hand-held medical suction device is provided having a vent orifice in the sidewall of the tip remote from the suction orifice of the tip and the hand holding portion of the device to regulate the negative pressure at the suction orifice. A fluid flow restriction orifice in the flow passage is disposed close to the vent orifice.

23 Claims, 1 Drawing Sheet

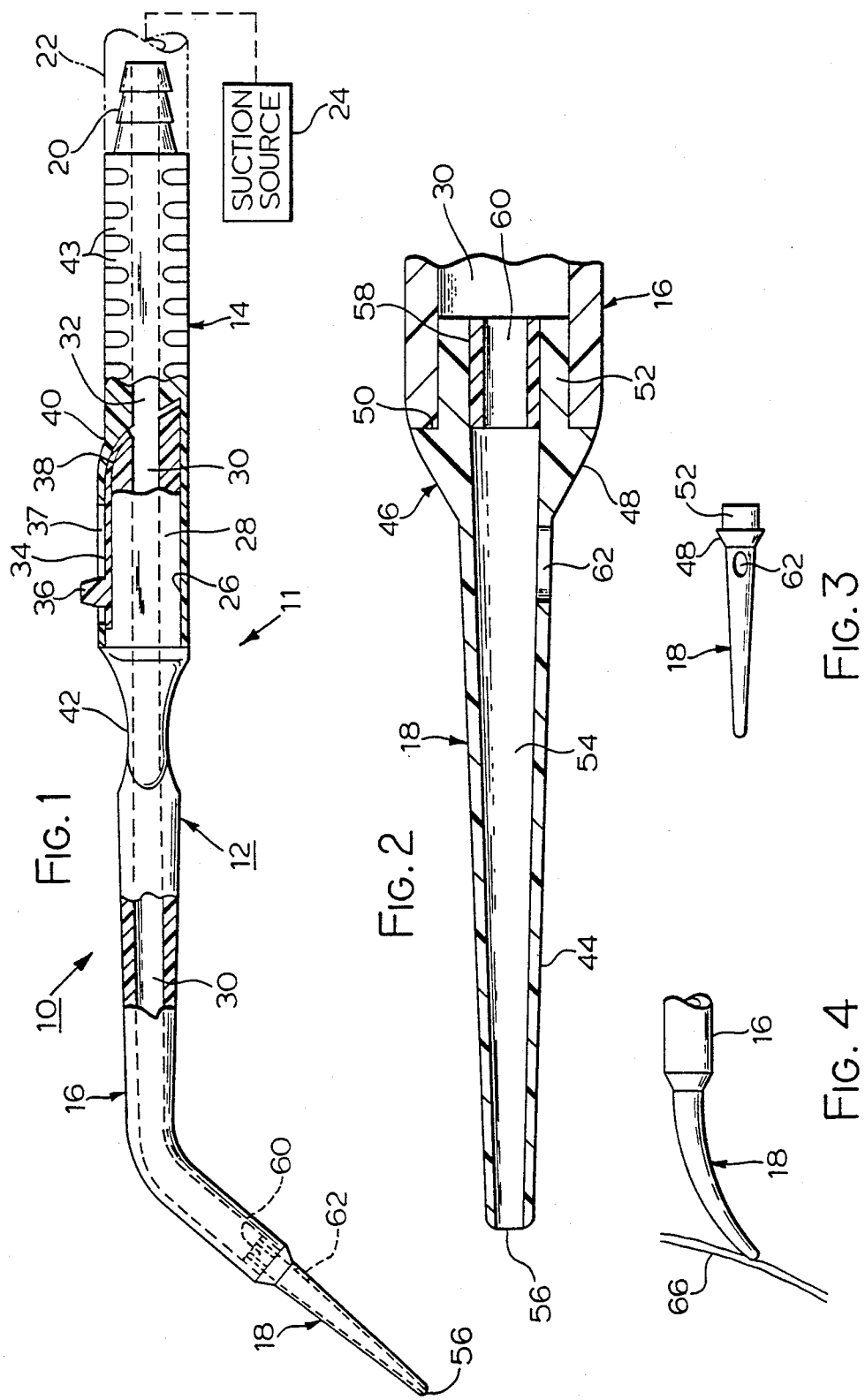

MEDICAL SUCTION DEVICE WITH AIR VENT AND FIXED RESTRICTOR

This is a continuation of co-pending application Ser. No. 881,374 filed on July 2, 1986 now abandoned.

TECHNICAL FIELD

This invention relates to medical suction devices and more particularly to hand held, fine tip suction devices.

BACKGROUND ART

Surgical suction devices, such as hand-held suckers, are used for removing blood and other body fluids from surgical sites, for example, to provide a clear view of the site during an operation. Where fine and delicate areas of the body are surgically involved, such as when delicate brain tissue, small veins, arteries, and nerves are operated on, for example, as when sutured, suckers having tips with suction orifices of small diameter are employed. The fine tips allow the accurate suctioning of very small amounts of liquid from selected areas.

With some suckers, it is possible to effect a high suction or negative pressure at the suction orifice when the orifice is occluded by body tissue. For example, when the suction orifice is occluded such that no liquid or air flows into the suction source, the negative pressure at the suction orifice increases to that of the source. Such a high pressure differential may, of course, cause excessive tissue grab and damage to occluding body tissue.

Some such suckers have suction tips of stainless steel with a suction orifice of small diameter. Such fine tips allow small quantities of liquid, such as small globules, of blood, to be removed from the site. However, because these tips are of rigid steel and of small diameter, there is the danger that inadvertent movement of the manually held sucker could readily damage delicate tissue.

Some suction suckers often produce relatively loud noises, such as gurgling sounds caused by the movement of air and liquid in the tip, as well as vibrations. Such vibrations are transmitted to the hand of the operator and this increases the difficulty of suctioning body fluids in small areas of the body.

SUMMARY OF THE INVENTION

It is therefore and object of the present invention to provide an improved hand-held medical suction device which reduces or substantially obviates one or more of the above-mentioned problems.

A more specific object of the present invention is to provide an improved hand-held, fine tip, medical suction device which automatically regulates or limits the maximum negative pressure at the suction orifice of the tip to values which are not damaging to body tissue when the suction orifice is occluded by body tissue.

Still another object is to provide an improved hand-held medical sucker having a fine tip and wherein noises and vibrations during operation of the sucker are substantially reduced.

In accordance with one aspect of the present invention, a sucker is provided that includes a body member having a hand holding portion and which is connectable with a source of suction, a suction tip is connected to the distal end of the body member and has a suction orifice at the distal end thereof. The device is provided with a vent to the atmosphere which is between and remote from the suction orifice and the hand holding portion of the body member to regulate the suction at the suction orifice. In accordance with another aspect, a flow resistance orifice is located adjacent the vent orifice with vent orifice between the suction orifice and the flow resistance orifice.

These as well as other objects and advantages of the present invention, will become apparent from the following detailed description and drawing.

BRIEF DESCRIPTION OF THE DRAWING

FIG. 1 is a side view, with portions broken away, of a medical hand-held suction device in accordance with a preferred embodiment of the present invention;

FIG. 2 is an enlarged longitudinal cross-sectional view of the distal end portion of the device of FIG. 1;

FIG. 3 is a bottom view of the tip of FIG. 1; and

FIG. 4 is a side view of a distal portion of the device of FIG. 1 illustrating the flexibility of the tip when bending forces are applied to it.

DESCRIPTION OF THE PREFERRED EMBODIMENT

Referring now to the drawing and particularly to FIG. 1, there is shown a medical suction device shown as a hand-held sucker 10 for aspirating body fluids such as blood from delicate areas of the body, such as encountered during brain operations or other operations where small and delicate body tissues, blood vessels, nerves, and the like are encountered. The sucker 10 includes a housing 11 including a body member 12 having a handle 14, and a probe 16, and a flexible tip 18 connected to the distal end of the probe 16. A generally conical serrated connector 20 integrally formed with handle 14 at the proximal end thereof is adapted to be connected to tubing such as indicated in phantom at 22 that connects device 10 with a a negative pressure or suction source indicated at 24 which may include a conventional or suitable body fluid collection container.

The handle 14 has a generally rectangular socket 26 at the distal end which receives a generally rectangular connector portion 28 of probe 16. The connector portion 28 may be fixedly connected in socket 26 of handle 14 by a suitable adhesive or the like. The probe 16 has a passageway 30 extending through it and which connects with a passageway 32 that extends through the handle 14. A flexible manually operated slide valve member 34 is slideable from a position in which the distal end of probe passage 30 is open and in fluid communication with the handle passage 32, as shown in FIG. 1, to a closed position in which the slide valve member 34 is moved proximally with the proximal portion of it moving downwardly to close off the proximal end of passage 30. The valve member 34 has a finger abutment 36 which extends through an opening 37 in the upper wall of the handle 14. The right or proximal end of valve member 34 is slideable between complementary facing surfaces 38 and 40 of the connector portion 28 and handle 14, respectively, to close and open fluid communication between the passages 30 and 32. Probe 16 is provided with four concave surfaces 42, one in each sidewall, so that diametrically opposed concave surfaces can be grasped between a thumb and index finger during use of the suction sucker 10, these surfaces serving to provide a comfortable part of the hand holding portion of the device for good handling and control. The hand holding portion of the device also includes parts of the handle 14 which is shown provided with hand engaging serrations 43. The probe 16 curves downwardly so that the distal end portion extends at an obtuse angle to the longitudinal axis of the other portions of the probe for ease of handling.

The suction tip 18, as also seen in FIG. 2, includes a main longitudinally extending generally conical or tapering portion 44 having an integral enlarged connector portion 46 at the proximal end. The connector portion 46 has a radially outwardly extending wall 48 ending in an annular, proximally facing flange 50 and a generally longitudinally extending tubular proximal end portion 52 that extends into the distal end of passage 30 of probe 16. The connector portion 46 of tip 18 is secured to the distal end of probe 16, for example, by suitable adhesive or other suitable means for securely fixing the end portion 52 to the walls of passage 30 of the probe 16. Tip 18 is provided with a longitudinally extending bore 54 extending through the tip and which is tapered or generally conical and extends radially outwardly in the proximal direction. Tip 18 at the distal end of passage 54 has a suction orifice 56. The tip is circular in cross-section with the diameter of passage 54 at the orifice 56 being smaller than that at any other point along the passage 54. The wall thickness slightly decreases from the connector portion 46 to the orifice 56. Since the main portion 44 is tapered, it provides even better vision of small areas of the site which are being aspirated.

A generally cylindrical fluid flow resistance member 58 is disposed in the cylindrical proximal end portion 52 of connector 46. Fluid flow restriction member 58 is secured in the tip portion 52, such as by a suitable adhesive. Flow resistance member 58 has a passage or flow resistance orifice 60 extending through it and having a smaller diameter than the diameter of passage 30, and a substantially larger diameter than that of suction orifice 56. The cylindrical portion 52 of tip 18 and the flow restriction member 58 with orifice 60 together provide a flow resistance effecting a fluid pressure drop and a fluid pressure differential between the suction source or passage 30 and passage 54 of the tip 18 so that the suction or negative pressure in tip passage 54 will be less than the suction or negative pressure in passages 30 and 32 of body member 12. The flow resistance orifice 60 is the most flow restrictive point in the device including tube 22 except for the relatively small suction orifice 56.

The sucker 10 is also provided with a vent opening or orifice 62 remote from both the suction orifice 56 and the hand holding portions of the body 12. Vent orifice 62 is shown formed in the sidewall of the tip 18 adjacent the proximal end of tip 18 and adjacent the flow resistance orifice 60 which is adjacent the prixmal end of the tip and distal end of the probe 16 in the illustrated embodiment. Vent 62 feeds ambient air into tip passage 54 which flows through the flow resistance orifice 60 into the passages 30 and 32 and tube 22 and then into the suction source 24. Vent orifice 62 regulates or maintains the suction across suction orifice 56 substantially constant even when orifice 56 is completely occluded, such as by body tissue or blood. Vent orifice 62 allows ambient air to be fed into the suction tip 18 and the suction system, and the amount of this air flow will vary as the negative pressure of the suction source 24 varies so as to regulate or maintain the suction at the suction orifice 56 substantially constant. Vent passage 62 is shown formed in the conical tip portion 44 at a point of relatively large diameter. Vent 62 is located on the bottom side of tip 18 as shown in FIGS. 1–3, that is, it is on the obtuse angle side of less than 180° or proximal side of the curved end portion of housing 11 so that there is less chance of inadvertently occluding vent 62 by engagement with body tissue.

The flow characteristics of the flow resistance orifice 60, vent orifice 62, and suction tip orifice 56, which are primarily determined by cross-sectional areas of these orifices, are so related that the suction or negative pressure at the suction tip orifice 56 is automatically maintained at a substantially constant relatively low level that cannot produce excessive tissue grab should the suction tip orifice 56 become occluded by body tissue. This of course is important in preventing body tissue damage especially where the sucker 10 is used in delicate areas of the body. Preferably, these orifices are related such as to provide a maximum grab force of, for normally expected variations in the negative pressure of the source 24, between about one-half gram and one and one-half grams, that is, such that the tip can raise a member having a weight of one-half to one and one-half grams if the member being lifted occludes the orifice 56.

The suction orifice 56 and outer diameter of the tip at the suction orifice should be small enough to permit good vision of the small areas of the body from which body fluid is to be removed.

A sucker made in accordance with the present invention and like that shown in the drawing had the following construction features:

Suction tip orifice 56 (circular): 0.0013 sq. in. (0.041 inch or 1.041 mm diameter)

Flow resistance orifice 60 (circular): 0.0053 sq. in. (0.082 inch or 2.083 mm diameter)

Vent orifice 62 (elliptical): 0.0094 sq. in. ( 0.12 inch 3.05 mm length, 0.10 inch or 2.54 mm width)

In this example sucker, the largest diameter of the tip passage 54, was approximately 0.124 inch (3.15 mm) in diameter and the length of the tip between flange 50 and the orifice 56 was about 1.48 inches (35.79 mm). The outer diameter of the tip at orifice 56 was about 0.095 inch (2.413 mm). The outer diameter of the tip at its junction with the enlarged connector portion 46 was about 0.21 inch (5.33 mm). The vent 62 was formed in the sidewall of the tip with the center of the vent 62 spaced proximally from the suction orifice 56 approximately 1.28 inches (32.51 mm). The length of the resistance member 58 and the cylindrical proximal end portion 52 of the tip were both about 0.2 inch (5.08 mm) in length and concentric with each other. The inner diameter of passage 30 of probe 16 was approximately 0.126 inch (3.20 mm) as also was the tubing, such as tubing 22, connecting the device 10 to the source of suction and fluid collection device. This example device produced a suction grab force about one-half gram when occluded even though there were variations in the negative pressure of source 24.

While the vent 62 is located remotely from the suction orifice 56, it is preferably placed somewhat close to the suction orifice but such that the suction orifice is not subject to closure by liquid or tissue during suctioning. By having the vent orifice 62 somewhat close to the suction tip orifice, only a relatively small column of liquid, such as blood, can be formed distally of the vent orifice or in passage 54 where the negative pressure is relatively low compared to that of passage 30. Since a column of blood is relatively small it can readily pass by the vent 62 and flow restriction 60 and flow into the high negative pressure passage 30 and through the device. If the vent and flow resistance orifices were located, too far (for example, 5 inches) from the suction orifice 56, it would be possible in a fine tip sucker for a substantially large column of liquid to fill that portion of the device distally of the vent passage thereby creating a column of liquid that may not be able to be drawn into the suction system past the vent because of the length and relatively low negative pressure of that distal portion of the device. Preferably, the vent orifice is at least one-half inch from the suction orifice 56 and less than two inches from the suction orifice.

The flow resistance orifice 60 should also be as close to the vent orifice 62 and tip orifice 56 as practical so as to avoid a relatively long portion of the flow passage through the device which is at a relatively low negative pressure. In other words, if the flow resistance orifice 60 was moved excessively proximally from the vent orifice 62 and orifice 56, there would be a considerable distance of passageway on the distal side of the resistance orifice 60 at which the negative pressure was relatively low so that liquid globules and could accumulate on the sidewalls instead of quickly passing through into the higher negative pressure passageways on the proximal side of the resistance orifice 60. In such a case, the liquid and air flow in such a low negative pressure passage would result in noise, such as gurgling sounds, and vibration. Such noise and vibration is reduced in the construction shown and described herein.

In the above example, the cross-sectional area of the vent orifice 62 was approximately twice that of the restriction orifice 60 and approximately seven times that of the suction orifice 56, and with the cross-sectional area of the restriction orifice being about five times that of the suction orifice tip. Preferably, the tip 18 has a suction orifice 56 which has a diameter that is less than 0.12 inch and more preferably, less that 0.05 inch. By making the orifice and the sucker tip small, the sucker tip can be moved into small areas of the body and the tip does not undesirably obscure the view of the operator when collecting small globules of liquid such as blood from small delicate tissues. The vent 62 is spaced far enough from the orifice 56 such that it will not enter pools of blood and such that there is little chance that it will be occluded by body tissue or blood. Since the vent orifice 62 is adjacent the enlarged connector portion 46, there is even less chance that it can be occluded during use. Also, with the vent orifice 62 located remotely from the hand holding portions of the member 12, it cannot be inadvertently closed by a finger or hand of the operator.

The effective area of the flow restriction orifice 60 should be substantially smaller than that of the vent orifice 62 in order to be effective in reducing suction in the tip passage 54. Because of the presence and relative size of the restriction orifice 60, the size of the vent orifice 62 may be desirably made small enough to avoid undesirably weakening the sidewalls of the fine tip 18. Both resistance and vent orifices are of fixed or predetermined size to provide consistent operation. Also, since the vent orifice 62 and the restriction orifice 60 are relatively close together and with the restriction orifice being only about an inch and a half from the suction orifice 56, only the relatively short passageway 54 will have a relatively low suction or negative pressure. Thus, fluids will have only a relatively short distance to travel before reaching the passage 30 of relatively high negative pressure. In the above example, the cross-sectional area of the passage 30 was about 0.035 sq. inch which was substantially larger than the vent and restriction orifices, the passage 30 being about seven times greater than that of the restriction orifice so that the restriction orifice 60 would have an effective reduction in the negative pressure of tip 18.

It will now be apparent that the use of the vent orifice 62 sufficiently remote from the suction orifice 56 so that body fluid and tissue do not come in contact with the external side of vent orifice 62, tends to regulate the suction or negative pressure differential across the suction orifice 56 upon the occurrence of an occlusion at the suction orifice 56 and thereby avoids damage to the tissue causing the occlusion. In other words, without the vent passage 62, any tissue occluding the orifice 56 would immediately result in the full suction force or negative pressure at the orifice being the same as that at the suction source since no air would flow in the system. The low suction at the tip also tends to reduce or prevent tissue grab during aspiration of blood.

The handle and probe may be made of a suitable, relatively rigid plastic material and may include plastic resins and copolymers and, for example, may include a acrylic copolymer or other suitable plastic. The valve slide 34 may be formed of a suitable flexible plastic such as polyethlyene. The fine tip 18 is preferably formed of a suitable flexible plastic material, for example, it may be formed of a polyvinyl chloride that is soft and flexible but which supports itself and is resilient enough to return to its original shape after being bent during use. The sidewalls of the tip 18 are normally straight, that is, without bending forces applied. FIG. 4 shows that the tip 18 engaging a small body surface and being bent. The tip 18, after being bent as in FIG. 4, is resilient enough to substantially return to its normally straight condition.

The vent orifice 62 is shown as a single opening in the sidewall of the tip 18, it being the only opening in the tip except for those at the distal and proximal ends of the tip. The effective orifice 62 may be formed by providing one or more openings where desired.

As various changes could be made in the above construction without departing from the scope of the invention, it is intended that all matter contained in the description or shown in the accompanying drawing shall be interpreted as illustrative and not in a limiting sense.

What is claimed is:

1. A hand-held fine tip sucker for suctioning body fluid from delicate areas of the body comprising housing means having a passage therethrough and including a handle adapted to be held in the hand for holding the sucker, and means at the proximal end thereof for connecting said passage with a suction source, a tip connected to the distal end of said housing means and having a passage therethrough connected with said housing means passage, said tip having relatively small suction orifice at the distal end thereof connected with said tip passage, said sucker having vent orifice means connecting said passages to the atmosphere and being disposed between and remote from said suction orifice and said handle, and fluid flow restriction orifice means of fixed size and position disposed in one of said passages between said vent orifice means and said handle in series flow relation with said passages for reducing the suction in said tip relative to that in said housing means passage, the flow resistance of said restriction orifice means being greater than that of said vent orifice means and less than said suction orifice.

2. The sucker of claim 1 wherein said vent orifice means includes a vent opening extending through the sidewall of said tip.

3. The sucker of claim 2 wherein said tip has a generally conical portion with said suction orifice at the narrow end thereof, and said vent orifice means is at the relatively large end of said conical portion.

4. The sucker of claim 1 wherein said fluid flow restriction orifice means has an effective cross-sectional area which is less than that of said vent orifice means.

5. The sucker of claim 4 wherein said tip is of plastic and said vent orifice means consists of a single opening extending through the sidewall of said tip.

6. The sucker of claim 4 wherein said flow restriction orifice is in said body member in said passage so related to size to said vent orifice means and said suction orifice that the suction force at said tip opening when suction is applied to said first passage is automatically limited to relatively low grab force values when occluded by body tissue.

7. The sucker of claim 4 wherein the effective cross-sectional area of said housing means passage is greater than the cross-sectional area of said flow restriction means.

8. The sucker of claim 4 wherein the effective cross-sectional area of said vent orifice means is greater than that of each of said flow restriction orifice means and said suction orifice.

9. The sucker of claim 8 wherein said restriction orifice is closely adjacent said vent orifice.

10. The sucker of claim 8 wherein said suction orifice has a cross-sectional area between about 0.001 and 0.002 of a square inch.

11. The sucker of claim 8 wherein the cross-sectional area of said flow restriction orifice is greater than that of said suction orifice, said suction orifice is a single opening at the distal end of said tip.

12. The sucker of claim 1 wherein said vent orifice means is disposed at least one-half inch from said suction orifice.

13. The sucker of claim 12 wherein said vent orifice means is spaced from said suction orifice between about one-half inch and two inches.

14. The sucker of claim 13 wherein said flow restriction means orifice means is about 0.2 inch from said vent orifice means.

15. The sucker of claim 1 wherein said housing means includes a distal end portion extending at an angle to an adjacent portion of said housing means and said vent orifice means is disposed on said distal end portion.

16. The sucker of claim 1 wherein said housing further includes a probe portion having a distal end portion extending at an obtuse angle to the longitudinal axis of said housing, and said vent orifice is in said tip on the side of the obtuse angle that is less than 180°.

17. The sucker of claim 1 wherein said flow restriction means is about one and one-half inches from said suction orifice.

18. The sucker of claim 1 wherein flow resistance of said flow restriction orifice means is substantially greater than the flow resistance of said vent orifice means.

19. A hand-held fine tip sucker comprising a body member including a probe having a first passage therethrough, and a handle having a second passage therethrough, the distal end of said handle being connected to the proximal end of said probe with said first and second passages connected in fluid communication, the proximal end of said handle having means for connecting said second passage with a source of suction, and a flexible tip having a third passage therein, the proximal end of said tip being connected to the distal end of said probe with said second and third passages connected in fluid communication, said tip having a suction orifice at the distal end thereof connected with said third passage, and vent orifice means extending through the sidewall of said tip for the flow of ambient air into said third passage, said vent orifice means being located remote from said suction orifice and closer to the proximal end of said tip than to the distal end thereof, and a flow resistance orifice of fixed size and position located proximally of said vent orifice means and adjacent the distal end of said probe in series flow relation with said passages, the effective cross-sectional area of each of said vent orifice means and said flow resistance orifice being greater than that of said suction orifice, the effective cross-sectional area of said vent orifice means being greater than that of said flow resistance orifice.

20. The sucker of claim 19 wherein said flow resistance orifice is located adjacent the juncture of said tip and said probe adjacent to but proximally of said vent orifice means.

21. The sucker of claim 20 wherein said probe and said handle have hand holding means thereon adapted to be grasped by the hand of an operator, said hand holding means being proximally remote from said vent orifice means.

22. The sucker of claim 21 wherein said body member has a switch thereon adjacent said hand holding portion for selectively opening and closing off fluid communication between said first and second passages.

23. The sucker of claim 19 wherein said flow resistance orifice is the most restrictive orifice in the device except for said suction orifice.

* * * * *